United States Patent [19]
Bare et al.

[11] Patent Number: 5,435,066
[45] Date of Patent: Jul. 25, 1995

[54] CUTTING DEVICE AND ASSEMBLY

[75] Inventors: Rex O. Bare, Lake Forest; Richard W. Hayob, Mission Viejo; Andrew J. Scherer, San Dimas, all of Calif.

[73] Assignee: M-Pact Corporation, Eudora, Kans.

[21] Appl. No.: 272,293

[22] Filed: Jul. 8, 1994

Related U.S. Application Data

[63] Continuation of Ser. No. 19,476, Feb. 18, 1993, abandoned.

[51] Int. Cl.$^6$ ............................................. B27B 9/00
[52] U.S. Cl. ....................................... 30/388; 30/516
[58] Field of Search ............... 30/390, 396, 398, 370, 30/166.3, 41.5, 43.7, 43.8, 43.9, 394, 516, 388; 83/602

[56] References Cited

U.S. PATENT DOCUMENTS

| | | | |
|---|---|---|---|
| 1,763,730 | 6/1930 | Von Lackum | 30/388 X |
| 2,371,535 | 3/1945 | McGuffin | 30/41.5 |
| 3,091,851 | 6/1963 | Cummins | 83/602 X |
| 3,224,305 | 12/1965 | Silver et al. | 30/41.5 X |
| 3,952,412 | 4/1976 | Rhodes | 30/166.3 |
| 4,081,906 | 4/1978 | Sigler | 30/390 X |
| 4,361,956 | 12/1982 | Kirk | 30/166.3 X |
| 4,379,362 | 4/1983 | Getto | 30/393 |
| 4,411,067 | 10/1983 | Kirk | 30/390 X |
| 4,543,718 | 10/1985 | Duescher | 30/124 |
| 4,544,293 | 10/1985 | Cranston et al. | 83/602 X |
| 5,014,430 | 5/1991 | Wortham | 30/166.3 |

FOREIGN PATENT DOCUMENTS 322599  11/1934  Italy ...................... 30/166.3

OTHER PUBLICATIONS

Brochure entitled "Introducing the Stryker 940 Cast Removal System," Dec. 1992, by Stryker Instruments, (4 pages).

*Primary Examiner*—Kenneth E. Peterson
*Attorney, Agent, or Firm*—Lyon & Lyon

[57] ABSTRACT

Provided is an ergonomic cutting device for cutting casts and other rigid objects comprising an oscillating cutting blade driven by a motor, a handle, and a vacuum system. The present cutting device is designed such that the offset positioning of the motor enables the weight of the motor to help manipulate and make more efficient the device. The vacuum system cools the device and draws dust produced by the cutting blade through the device without contacting the dust with the motor or other mechanical components. The motor is designed to initially engage in an idle mode when the device is turned on, then automatically sense when a load is placed on the cutting blade and, at that point, boost to a cutting mode. The motor may also be manually placed in a higher powered turbo mode. The device also includes a dynamic braking system which enables the device to stop oscillation of the blade faster than previous device.

20 Claims, 10 Drawing Sheets

CUTTING DEVICE AND ASSEMBLY

This is a continuation of application Ser. No. 08/019,476, filed on Feb. 18, 1993, now abandoned.

FIELD OF INVENTION

The present invention relates to cutting devices, particularly devices for cutting casts and the like.

BACKGROUND

Presently, there is a need for cutting casts and other rigid objects (e.g. helmets, dry wall, bone or frozen material, etc.). For example, casts are rigid dressings which are used to immobilize broken bones and the like. Casts may be made from materials such as plaster or layered fiberglass set with resin. Generally, removal of such rigid casts requires use of some cutting device.

Any cutting requires relative motion between the material being cut and a blade. Normally this is achieved by rotating the blade or moving the blade in long linear strokes. For example, industrial cutting devices of the past have most often used rotating or reciprocating blades to cut through rigid materials such as plaster or fiberglass/resin material, but such cutting modes are generally considered too dangerous for use in removing casts from patients due to the close proximity of the cast to the patient. Such cutting blades can also be dangerous to the user. Therefore, a preferred action is one which provides relatively short oscillating strokes of a blade. Instead of rotating or reciprocating blades, medical cutting devices typically use oscillating serrated or toothed blades which are considered safer.

In theory, oscillating blades with a relatively small angle of oscillation (e.g. less than 15°) show relatively little tendency to cut skin or soft tissues (i.e. soft low mass materials) since these materials tend to move or jiggle along with the blade movement rather than be cut (i.e. eliminating the relative motion required for cutting). More rigid materials with greater mass tend to remain stationary and, thus, allow the relative motion required for cutting. Rigid materials with appreciable mass, including plaster and multi-layer fiberglass casts, are readily cut using an oscillating blade operating at motor speeds of 12,000-20,000 rpm. The best cutting performance is typically obtained at higher speeds, particularly speeds which are above the resonant frequencies of typical cast materials.

The relative motion between the materials being cut and the serrated or toothed blade is reduced by the friction between the two causing the material being cut to move with the blade and the cutting device driving the blade to oscillate opposite the blade ("friction movement") thereby reducing the blade's relative movement and efficiency. This friction movement is preferably minimized because it reduces the efficiency of the cutting device and adds to the fatigue of the user. Cutting devices of the past suffer from significant inefficiency due to friction movement.

Cutting devices generally include a motor, a handle and a cutting blade. Devices of the past are both bulky and poorly designed from ergonomic and efficiency perspectives. Generally, the motors used in such devices are heavy, noisy, and may produce excessive heat. Many devices use line-voltage A/C brush-type motors that require fans and open air vents to provide sufficient airflow to cool the motor during use. This configuration is inherently noisy, relatively inefficient, and cutting residue and dust may be drawn into the motor and other components by the necessary flow of cooling air.

In addition, such devices have typically been designed with the motor positioned in-line with the handle and cutting blade positioned linearly along the handle whereby the handle is between the cutting blade and the motor (i.e. the weight of the motor is generally behind the hand position on the handle (opposite the cutting blade) when the device is used to cut). This design provides a device which is not balanced and has a low moment of inertia with which to resist the device's tendency to oscillate opposite the blade. Therefore, devices with this design are difficult to use and are inefficient at cutting. Still other devices are designed with the motor positioned encased within the handle. This design provides a device which is bulky to hold and, therefore, is difficult to use. In addition, these devices tend to be under powered, are not balanced and have a low moment of inertia with which to resist the device's tendency to oscillate opposite the blade. Furthermore, the heat generated by the device is usually conducted to the handle which is uncomfortable to the user and even to the patient.

The general method of use of such cutting devices is to plunge-feed the cutting blade into, through, and out of the cast (or other rigid material) at a first static location and then repeat the in, through, and out procedure at second, third, . . . etc. locations. Each cut results in a single elongated slot puncture in the cast. The cast is easily removed once a lengthwise cut is formed by stringing together a plurality of such single cuts. The design of prior cutting devices, explained above, wherein the motor and cutting blade are on opposite ends of a handle, results in one end of the cutting device being much heavier than the other end. This lack of balance makes the device difficult to control and use, since the cantilevered weight of the motor must be supported and resisted by the user's wrist muscles.

To provide an oscillating blade, most cast cutting saws of the past have used a "Y" shaped yoke, an eccentric cam attached to a shaft of the motor (which typically extends through the handle) and positioned between tines at the forked end of the yoke, and the cutting blade attached to a stem at the opposite end of the yoke. As the motor rotates the eccentric cam, the forked end of the yoke moves from side-to-side which, in turn, moves the stem end of the yoke thereby oscillating the cutting blade (usually between 5°-20°). Thus, rotational movement of the eccentric cam is translated into oscillating movement of the cutting blade.

For these types of cutting devices the eccentric cam must be sized to precisely fit between the tines. If there is space between the cam and the tines, the device will be noisy when in use. The loudness of the device is important because it both frightens patients and hinders communication. However, if the eccentric cam precisely fits the space between the tines, thereby minimizing noise production, the friction between the eccentric cam and the tines will produce heat. Heat production is a problem because, depending on the materials involved, the heat could be conducted back to the motor, through the handle, or down to the cutting blade. If heat is conducted to the motor, it could have adverse effects including shortening the life of the motor. If heat is conducted through the handle or to the cutting blade, it could result in burning the user or the patient if they come into contact with either the handle or the cutting blade.

A further problem of these prior devices is they lack braking mechanisms and merely allow the blades of these devices to rotate or oscillate several hundred cycles before coming to a full and complete stop. This can take up to several seconds. A better braking mechanism is needed.

An additional problem is the removal of cutting residue and dust which is created when the cast or other rigid object is cut. Some cutting devices of the past have included vacuum systems to help collect such residue and dust. However, these vacuum systems have not been integral parts of the cutting device. Rather, they have tended to be clumsy attachments which are awkward and inefficient. In addition, these vacuum systems do not typically provide unobstructed vacuum passageways and, therefore, suffer inefficiencies in removing cutting residue or dust.

In general, prior cutting devices suffer from excess noise, heat build-up, inefficiencies, poor design and weight distribution, and/or operate at speeds and power levels that are less than optimal for the materials they are expected to cut.

SUMMARY OF INVENTION

The present invention comprises a cutting device which solves the problems of the prior cutting devices. A preferred embodiment of the present invention comprises a newly designed cutting device which is easier to handle than the prior devices. The design of the present cutting device places the motor offset from the handle (i.e. generally above the hand position on the handle when the device is used to cut) such that the weight of the motor actually helps, rather than hinders the user This offset positioning of the motor relative to an axis-of-rotation (i.e. an axis about which the cutting device tends to rotate or oscillate, particularly, the cutting blade shaft) helps to counteract the tendency of conventional cutting devices (especially the lighter weight devices) to vibrate under load (i.e. friction movement). As is explained above, much of the blade cutting action of prior cutting devices is lost when these devices, due to improper placement of mass, begin to oscillate around the axis-of-rotation. As is also explained below, placement of a mass off-set from the axis-of-rotation (i.e. increasing the moment of inertia) minimizes this effect. In addition, the positioning of the motor in the present cutting device prevents heat produced by the motor from being conducted to the handle of the device.

Furthermore, the mechanics of the present cutting device are improved over the prior devices. Rather than having a tined yoke to translate rotation to oscillation, as do many of the prior devices, the present device uses a rod and crank design which minimizes both noise and friction (i.e. heat production).

To further minimize noise and maximize motor life-span, the motor of the device is designed to initially engage in an "idle" mode when the device is turned on, then automatically "sense" when a load is placed on the cutting blade and at that point boost to a "cutting" mode. In addition, the motor may be manually boosted further and placed in a "turbo" mode. This allows the user to further increase the cutting power of the motor at their discretion.

Accordingly, it is an object of the present invention to provide an improved cutting device.

It is an object of the present invention to provide a cutting device for cutting casts and other rigid objects which is more efficient than the devices of the past.

It is a further object of the present invention to provide a cutting device which is quieter and yet more powerful than the devices of the past.

It is also an object of the present invention to provide a cutting device which is better designed in that it is balanced and easier to use than the devices of the past.

It is an additional object of the present invention to provide a cutting device which includes features to maximize the life-span of the device components.

It is yet another object of the present invention to provide a cutting device which is safer than the devices of the past.

Other objects and features of the present invention will become apparent from consideration of the following description taken in conjunction with the accompanying drawings.

DETAILED DESCRIPTION OF THE PREFERRED EMBODIMENT

Figure 1A:
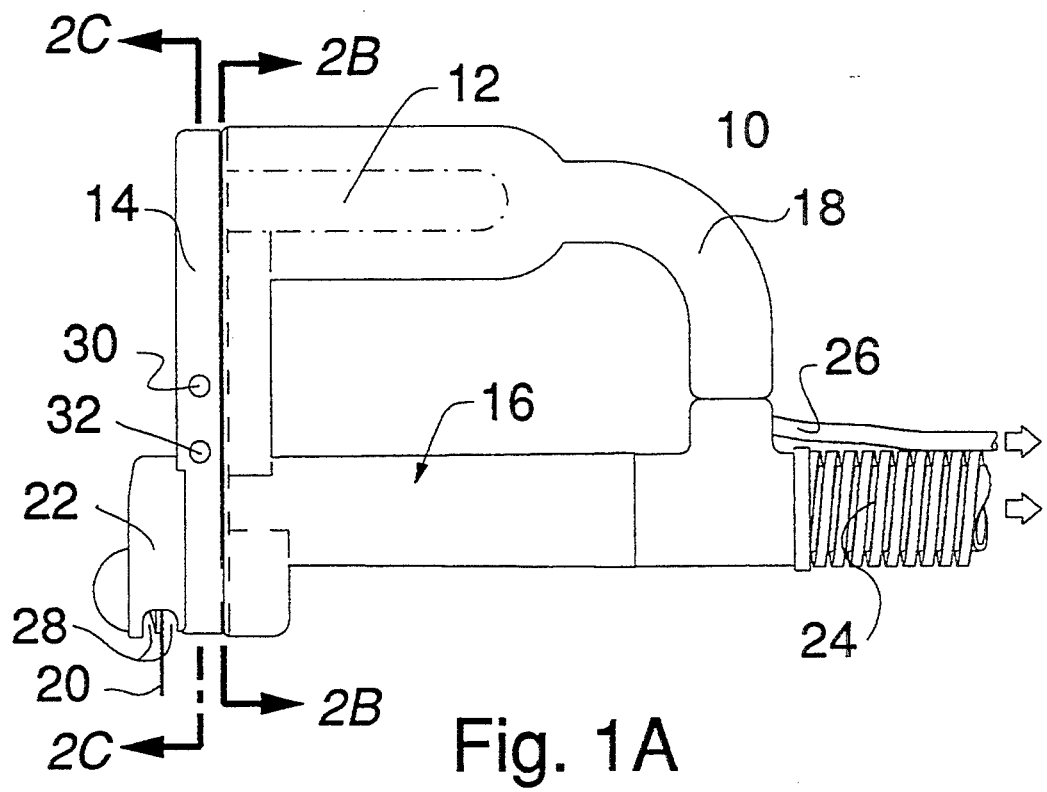
FIG. 1A is a side view of a cutting device according to the present invention.
Figure 1B:
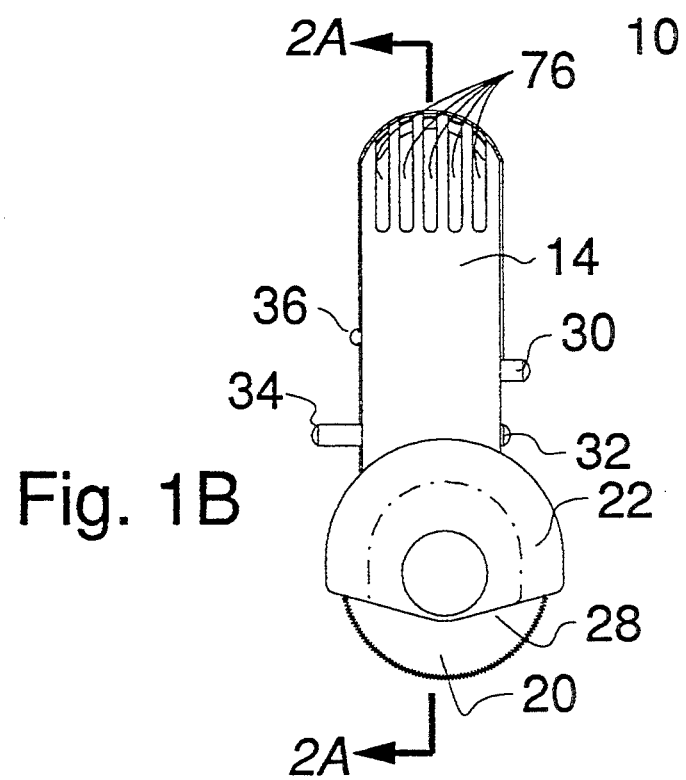
FIG. 1B is a front view of the cutting device of FIG. 1A.

Turning now to the drawings, FIGS. 1A and 1B show side and front views, respectively, of a preferred embodiment of the cutting device 10 of the present application. As shown in FIG. 1A, the cutting device 10 includes a motor housing 12, a front housing 14, a handle 16, and a vacuum hose annex 18, all positioned to outline a generally rectangular shape with the motor housing 12 and the handle 16 forming a top and bottom of a rectangle, respectively, and the front housing 14 and vacuum hose annex 18 forming sides or ends. Approximate the junction of the front housing 14 and the handle 16 is a serrated circular cutting blade 20 which is partially encased in a blade guard 22. The cutting blade 20 oscillates about an axis through an angle between approximately 5°–15° (preferably 10°) to thereby cut through rigid objects.

The generally rectangular design provides the motor housing 12 (which, as will be described below, encases a motor 70 (see FIG. 2A)) in a position off-set from the handle 16 (i.e. the motor is located generally above the hand position on the handle when the device is positioned to cut). This off-set positioning helps minimize the friction movement problems of the prior art devices described above.

As was described above, the relative motion (i.e. the cutting action) between materials being cut and a blade is reduced by the friction between the two causing the material being cut to move with the blade and the cutting device driving the blade to oscillate opposite the blade thereby reducing the blade's movement and efficiency. The moments of inertia (i.e. the distribution of the masses relative to the movement) of both the material being cut and the cutting device driving the blade resist this tendency to move due to friction (i.e. "friction movement"). Thus, if the moments of inertia are higher, the friction movement is lower. In addition, if the speed of the oscillation is higher, the moment of inertia is better able to resist the friction movement.

With regard to the friction movement of the material being cut, since the mass of the material being cut and distribution of the mass are fixed, its friction movement can be adjusted only by adjusting the speed of oscillation of the blade. With regard to the friction movement of the cutting device driving the blade, the mass of the cutting device is preferably minimized (e.g. for ease of use and user comfort reasons), but once the speed of the oscillation is adjusted, the friction movement of the cutting device may be further reduced by distributing its mass so as to produce the highest moment of inertia possible without unnecessarily increasing its mass.

The highest moment of inertia is produced by placing as much of the mass as possible as far from the axis of rotation of the device as possible. The axis of rotation of the present device 10 is the rotational axis (i.e. the shaft) of the cutting blade 20. Therefore, the moment of inertia of the cutting device 10 can be maximized by off-setting a mass away from the shaft of the cutting blade 20. Since the motor 70 of the device 10 is a major source of mass of the device 10, off-setting the motor 70 away from the shaft of the cutting blade 20 will increase the moment of inertia of the device 10 without adding unnecessary additional weight. However, as explained above, the moment of inertia of the device 10 can be increased by off-setting any mass away from the rotational axis of the device.

All prior cutting devices have positioned their motors right on or very near (within approximately an inch) the axis of their blade shafts. The positioning of the motor in prior devices not only results in a lower moment of inertia, but also, as described above, results in unbalanced design and providing a major heat source in close proximity to the handle and, therefore, to the user's hand. The off-set design of the present cutting device 10 (off-set approximately 3–6 inches and preferably 4.5 inches between the motor 70 shaft axis and the cutting blade 20 shaft axis) results in a moment of inertia many times greater for a device of a given weight when compared to the design of the prior devices and, therefore, greatly reduces friction movement of the cutting device 10 and enhances the device's efficiency and ease of use.

In general, if the power of the cutting device is higher, the moment of inertia must be higher to counteract the resultant friction movement. The off-set design of the present device 10 allows for the highest power for a given weight. In addition, the off-set design enables the weight of the motor 70 to be centered or balanced at a point in close proximity to the handle 16 and, therefore, to the user's hand. This provides the user with greater control over the device 10 and renders the device 10 easier to use. Furthermore, the off-set design keeps the heat of the motor 70 away from the handle 16 and, therefore, away from the user's hand.

Turning back to the drawings, as seen in FIG. 1A, approximate the junction of the handle 16 and the vacuum hose annex 18 is a vacuum hose 24 and a power cable 26. The vacuum hose 24 enables a negative pressure to be supplied to draw air through the cutting device 10 from an inlet 28 in the blade guard 22 and through air channels 76 (FIGS. 1B, 2A, 2B, and 2C) in the motor housing 12 and front housing 14 (this process is described in detail below). The power cable 26 enables power to be supplied to a motor (described in detail below) encased in the motor housing 12.

Also shown in FIGS. 1A and 1B, the front housing 14 includes a variety of power buttons: an "off" button 30, an "on"/"kill" button 32/34 (FIG. 1B), and a "turbo" button 36 (FIG. 1B). These buttons 30, 32, 34, and 36 are all connected to switches and are all described in more detail below.

Figure 2A:
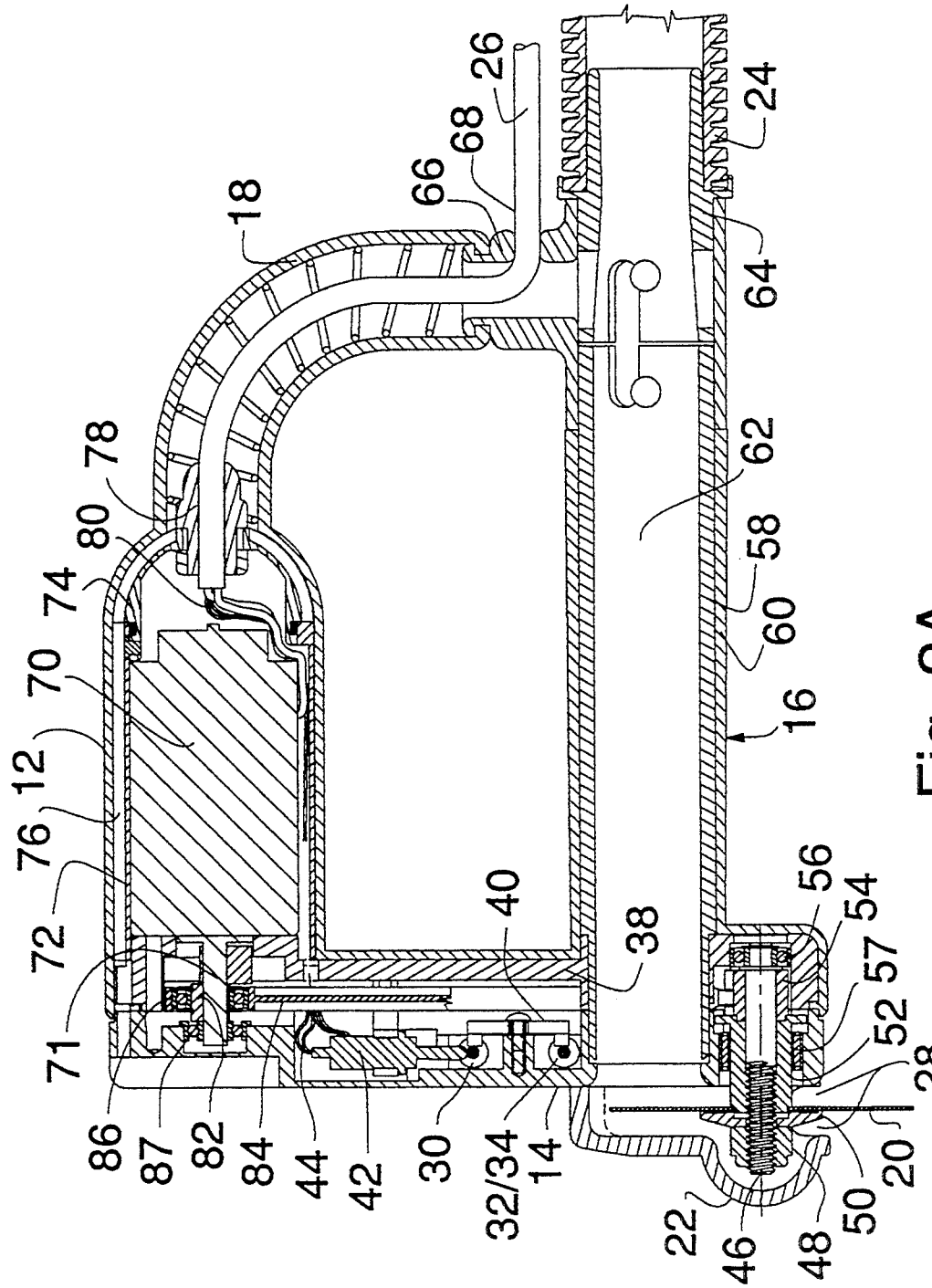
FIG. 2A is a cross-sectional view of the cutting device taken along line 2A—2A in FIG. 1B.
Figure 2B:
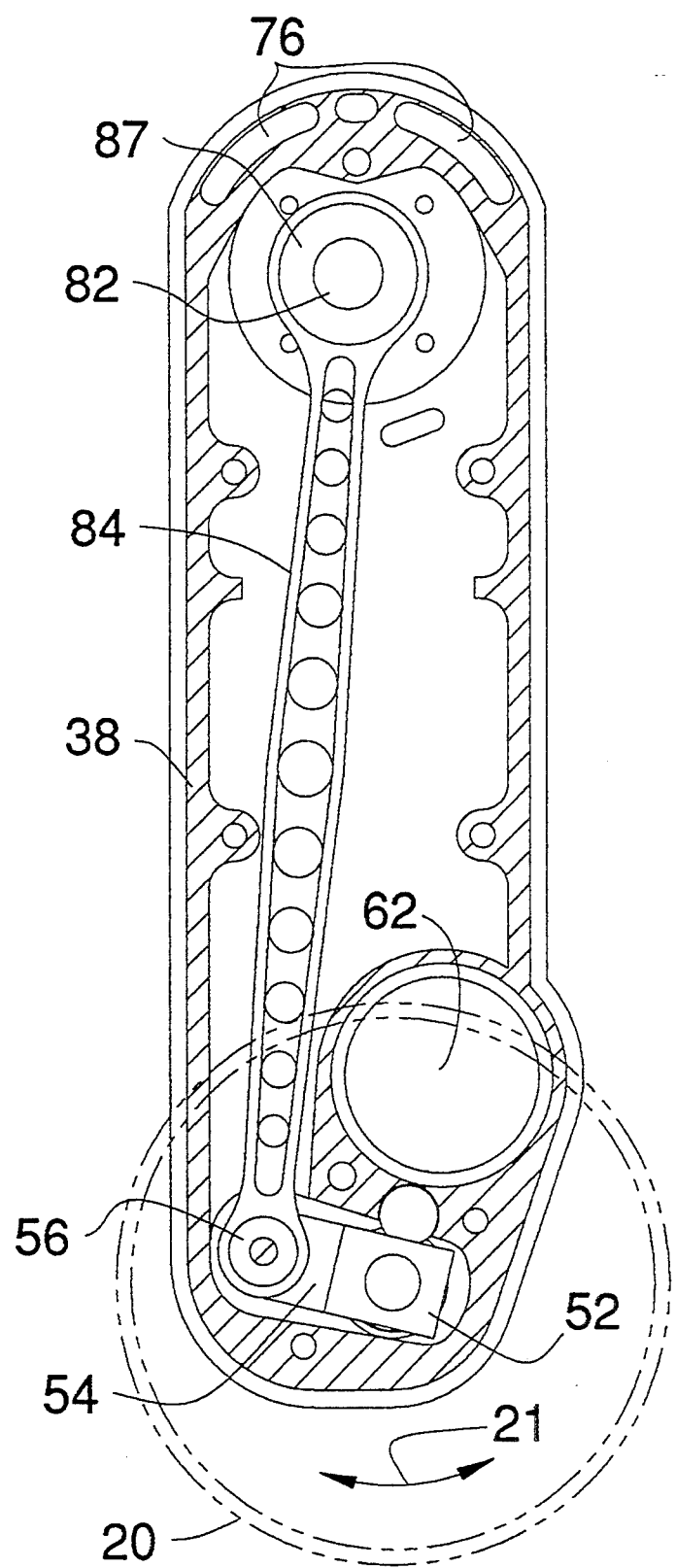
FIG. 2B is a cross-sectional view of the cutting device taken along line 2B—2B in FIG. 1A.
Figure 2C:
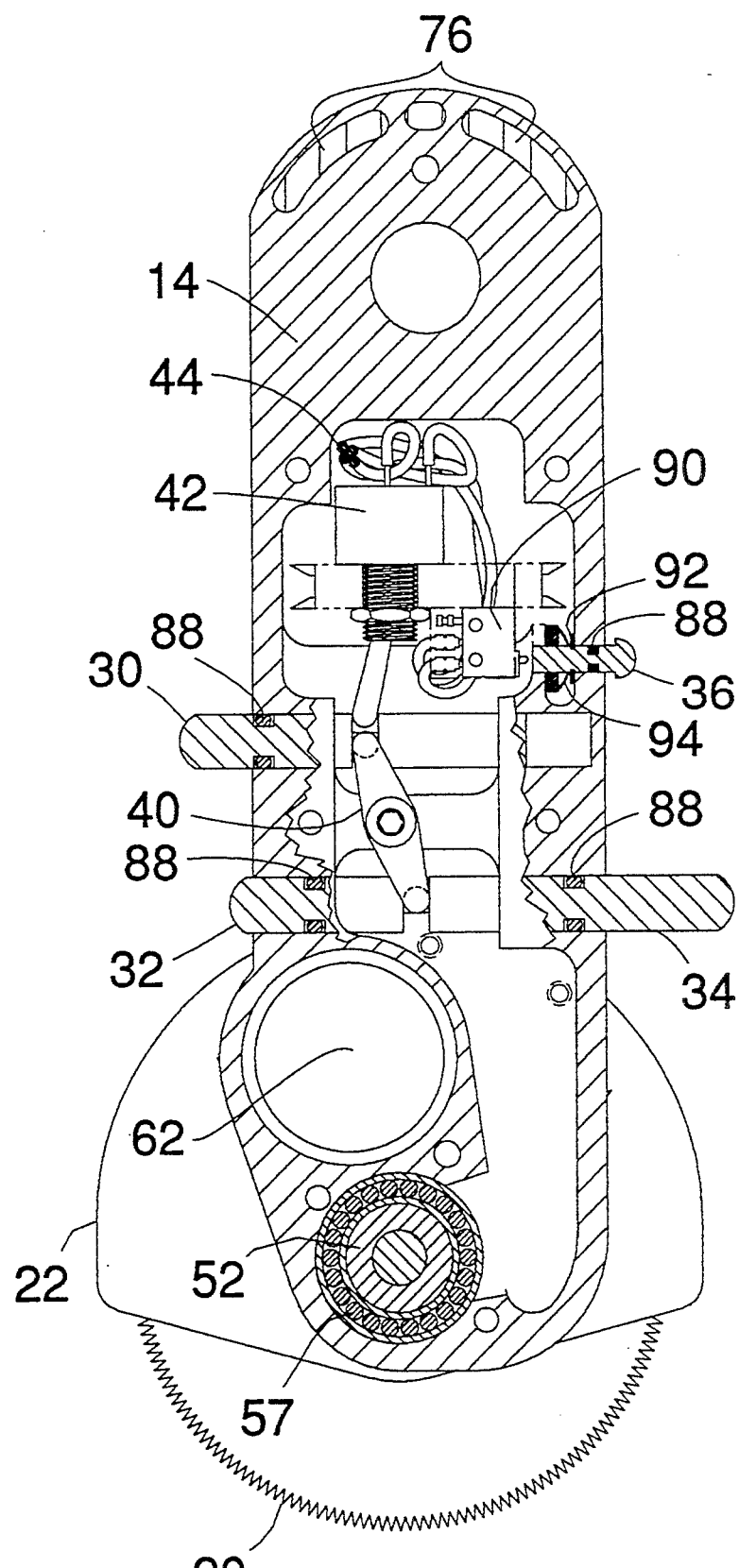
FIG. 2C is a cross-sectional view of the cutting device taken along line 2C—2C in FIG. 1A.

As shown in FIGS. 2A, 2B and 2C cross-sectional views of the present cutting device 10 reveal the inner construction of the cutting device 10. FIG. 2A shows a cross-sectional side view through the cutting device 10. Many of the exterior features shown in FIG. 1A are also shown in FIG. 2A, particularly: the rectangularly positioned motor housing 12, front housing 14, handle 16, and hose annex 18. The cutting blade 20, blade guard 22, vacuum hose 24, power cable 26, and inlet 28 are also shown. FIG. 2A shows details of the interior components of the present device.

A rear housing 38 is shown in FIG. 2A as interior to the rectangle and generally extending between the motor housing 12 and the handle 16. The rear housing 38 together with the front housing 14 encase electrical and mechanical components of the cutting device 10, particularly the off button 30, the on/kill button 32/34, a bell crank 40 and a switch 42 which are mechanically coupled to the buttons 30, 32, and 34 (described in detail below). Control wires 44 are connected to the switch 42 and feed back through the power cable 26. These components are encased within the front and rear housings 14 and 38 which protect the components from exposure to dust of other possible contaminants (e.g. residue, liquids, cleaners, etc.). The front housing 14 is removable thereby providing easy service access to these interior components of the cutting device 10.

The blade guard 22 partially encases the blade 20. Shown in FIG. 2A, the blade 20 is attached to the cutting device 10 by means of a threaded bolt 46, nut 48, and washer 50 arrangement. The bolt 46 is attached to a crank end 52 which is coupled to a crank 54 (described in detail below) both of which are integral with the cutting device 10 and are supported by crank bearings 56 and 57.

As shown in FIG. 2A the handle 16 comprises a hollow handle shell 58 which is covered or coated with a hand grip 60. The hollow interior of the shell 58 provides an unobstructed vacuum passage 62 to enable air to flow therethrough which also keeps the handle 16 cool and collects dust and other cutting residue generated by the cutting blade 20. The vacuum hose 24 connects to the vacuum passage 62 via a hose adaptor 64. One end of the vacuum hose annex 18 connects to the vacuum passage 62 via a handle adaptor 66 which also provides an inlet portal 68 for the power cable 26. The power cable 26 is threaded through the vacuum hose annex 18 to the motor housing 12.

The other end of the vacuum hose annex 18 is coupled to the motor housing 12. As shown in FIG. 2A, the motor housing 12 encases a motor 70 which is covered with a motor heatsink 72 and is capped with a motor endcap 74. The motor 70, heatsink 72, and endcap 74 are sized such that they fit within the motor housing 12 leaving space for an air channel 76 which extends from the front housing 14 and couples to the vacuum hose annex 18. The air channel 76 enables air to be drawn in through the front housing 14, over the heatsink 72 and out the vacuum hose annex 18 thereby cooling off the motor 70. The airflow through the motor housing 12 is separate from the airflow through the handle 16 (which collects dust and other cutting residue). Thus, exposure of the motor 70 to dust or other contaminants is minimized. The motor endcap 74 provides the power cable 26 access into the motor housing 12 via a cable clamp 78. The endcap 74, clamp 78, and cable 26 are all coupled to seal the motor 70 within the heatsink 72. The cable 26 holds both power wires 80 for the motor 70 and the control wires 44 for the switch 42.

The motor 70 is preferably a D.C. motor. For example, a permanent (neodymium) magnet D.C. motor such as motor model number 35NT2R82-426 P.2 from Escap, Switzerland. Having a D.C. motor provides the device 10 with more power (i.e. torque) for its size and weight, is more efficient (i.e. produces less heat for the same power when compared to an A/C motor), provides better speed control, and is safer due to requiring only a lower voltage D.C. power.

As will be described in detail below, a rotary shaft 71 of the motor 70 is coupled to an eccentric cam 82 which is coupled to a connecting rod 84 which is coupled to the crank 54 (which is coupled to the blade 20). The cam 82 and the rod 84 are supported by bearings 86 and 87 which provide a low friction close fit. The cam 82, rod 84, and crank 54 arrangement enables the motor 70 to oscillate the blade 20.

The hand grip 60, described above, preferably comprises a rubberized material (preferably a closed-cell pvc foam) and preferably extends over exterior surfaces of the handle 16, the vacuum hose annex 18, and the motor housing 12. Thus, the hand grip 60 not only provides a good gripping surface for the handle 16, but also provides noise dampening which reduces the noisiness of the cutting device 10 and provides a thermal barrier that protects the user and others, including the patient, from any build-up of heat (e.g. from the motor or other sources) on those exterior surfaces. The hand grip 60 need not be provided on devices 10 wherein the rubberized material may become contaminated or uncleanable (e.g. autopsy uses).

FIG. 2B shows details of the cam 82, rod 84 and crank arrangement. The eccentric cam 82 and support bearing 87 fit within a circular fitting at a first end of the connecting rod 84. A pivot shaft of the crank 54 and crank bearing 56 fit within another circular fitting at a second (and opposite) end of the connecting rod 84. As the motor 70 turns the eccentric cam 82, the first end of the connecting rod 84 is correspondingly moved. This movement is translated to the second end of the connecting rod 84 and enables the crank 54 to move the blade 20 in a back-and-forth, saw-like oscillating motion as shown by arrow 21 in FIG. 2B. It is this oscillating motion of the blade 20 which enables cutting of casts or other rigid objects. The length of the connecting rod 84 provides the present device 10 with an efficient angle to drive the cutting blade 20. As shown in FIGS. 2A and 2C, it is actually the crank end 52 which is coupled to the cutting blade 20. The bearings 56, 57, 86, and 87 all provide support and provide a low friction close fit between the various members. This low friction close fit at all points in the drive mechanism enables quieter and cooler operation of the cutting device 10 when compared to the prior yoke-arrangement devices.

FIG. 2C also shows details of the switching system of the cutting device 10. As shown in FIG. 2C, the buttons 30, 32, and 34 are all mechanically coupled to the switch 42 and the turbo button 36 is mechanically coupled to the turbo switch 90. The switches 42 and 90 are, in turn, connected to the control wires 44 and control the state of the cutting device 10 as in "on"/"idle," "off," "normal cutting," or "turbo" mode.

The buttons 30, 32, and 34 are all mechanically coupled via a bell crank 40 such that when the on button 32 is pushed in, the off and kill buttons 30 and 34 respectively are pushed out and vice versa. This button arrangement allows for easy push button operation of the cutting device 10 and provides the safety feature of turning off the cutting device 10 when it is laid (on the right side as seen in FIG. 2C) on a surface while in the "on" mode. The switch buttons 30, 32, 34, and 36 are all sealed to the front housing 14 via button O-rings 88.

The buttons 30, 32, 34, and 36 allow the user to control the operating mode of the cutting device 10 from a location on the cutting device 10 itself. The on button 32 turns the cutting device 10 on in its regular mode such that it may switch between idle and normal cutting modes (described below). The off and kill buttons 30 and 34 turn it off. The turbo button 36 allows the user to choose to place the cutting device 10 in a turbo mode which provides an additional surge and increased level of power to the motor 70 and, thus, to the cutting blade 20, as compared to the normal cutting mode. Pressing the turbo button 36 toggles an electronic flip-flop divider in a voltage control 132 (described below). This arrangement enables the turbo mode to be engaged (i.e. turned on) when the turbo button 36 is depressed and then disengaged (i.e. turned off) when the turbo button 36 is depressed a second time. As shown in FIG. 2C, the turbo button 36 arrangement includes a retaining device 92 and a spring 94. The retaining device 92 and spring 94 bias the button 36 to be in a raised position.

As mentioned above, the preferred embodiment of the present cutting device 10 has several power modes: "off," "on/idle," "normal cutting," and "turbo." When a user first turns the cutting device 10 on, the motor 70 is powered to "idle." When the motor 70 is powered to idle it is at a slow speed and is not very noisy. When the user starts to cut the need for increased power is sensed (as described in detail below) and full normal cutting power is provided to the motor 70 (enough to cause the cutting blade 20 to oscillate between approximately 10,000-20,000 and preferably 15,000-16,000 cycles per minute). The user may require extra power or speed (in excess of the normal cutting power). The user may optionally switch the motor 70 into a "turbo" mode by depressing the button 36 and thereby providing the motor 70 with an even higher power level (enough to cause the cutting blade 20 to oscillate at more than 16,000 and preferably 18,000-19,000 cycles per minute). While the cutting device 10 is in the turbo mode and the user stops cutting, the device 10 will return to an idle mode (which sounds different than the initial and normal cutting power idle mode thereby enabling the user to determine, while in idle, which mode the cutting device 10 is in). However, if the cutting device 10 is shut off, then, after a delay (e.g. 10 seconds), an automatic reset will reset the cutting device 10 back to the normal mode (i.e. normal idle when initially turned on switching to normal cutting mode upon sensing a load).

When full normal cutting power (or turbo power) is provided to the motor 70, a vacuum 100 is also automatically turned on to cool the device 10 and to remove any dust or other residue which is created from the cutting action (this is described in detail below). The vacuum 100 includes an electronic soft start which provides for a gradual turning on of the vacuum 100 so as to minimize current surges through the device 10 and to minimize the noise level when the device 10 goes into a cutting mode (e.g. either normal cutting or turbo modes). When the user stops cutting the motor 70, after a delay (preferably between 1–10 seconds), will return to idle (and the vacuum 100 will turn off). Thus, the vacuum 100 is automatically turned on only when it might be needed (i.e. only when the device 10 is in either a normal cutting mode or a turbo mode) and automatically turns off when it is not needed (i.e. when the device 10 is in an idle mode (either normal or turbo)).

The present cutting device 10 may include a dynamic braking system such that when the cutting device 10 is turned off (i.e. is switched to "off" using buttons 30 or 34) the dynamic braking system enables the motor 70 to stop rotation and, therefore, stop oscillation of the cutting blade 20 within approximately 1–10 revolutions (preferably 2–5 revolutions). This provides increased safety and convenience in using the present cutting device 10. Prior cutting devices may require several hundred revolutions prior to stopping thereby taking several seconds.

The various levels of power supplied to the motor 70 have a variety of benefits. One benefit, for example, is that the motor 70 will have a longer life-span because it is only at a higher working power when it is actually needed for cutting. Another benefit is that the idle mode provides a quiet "on" mode so the user can get situated and the patient can become more comfortable with the cutting device 10. In addition, some light cutting can be done in the idle mode.

Figure 3:
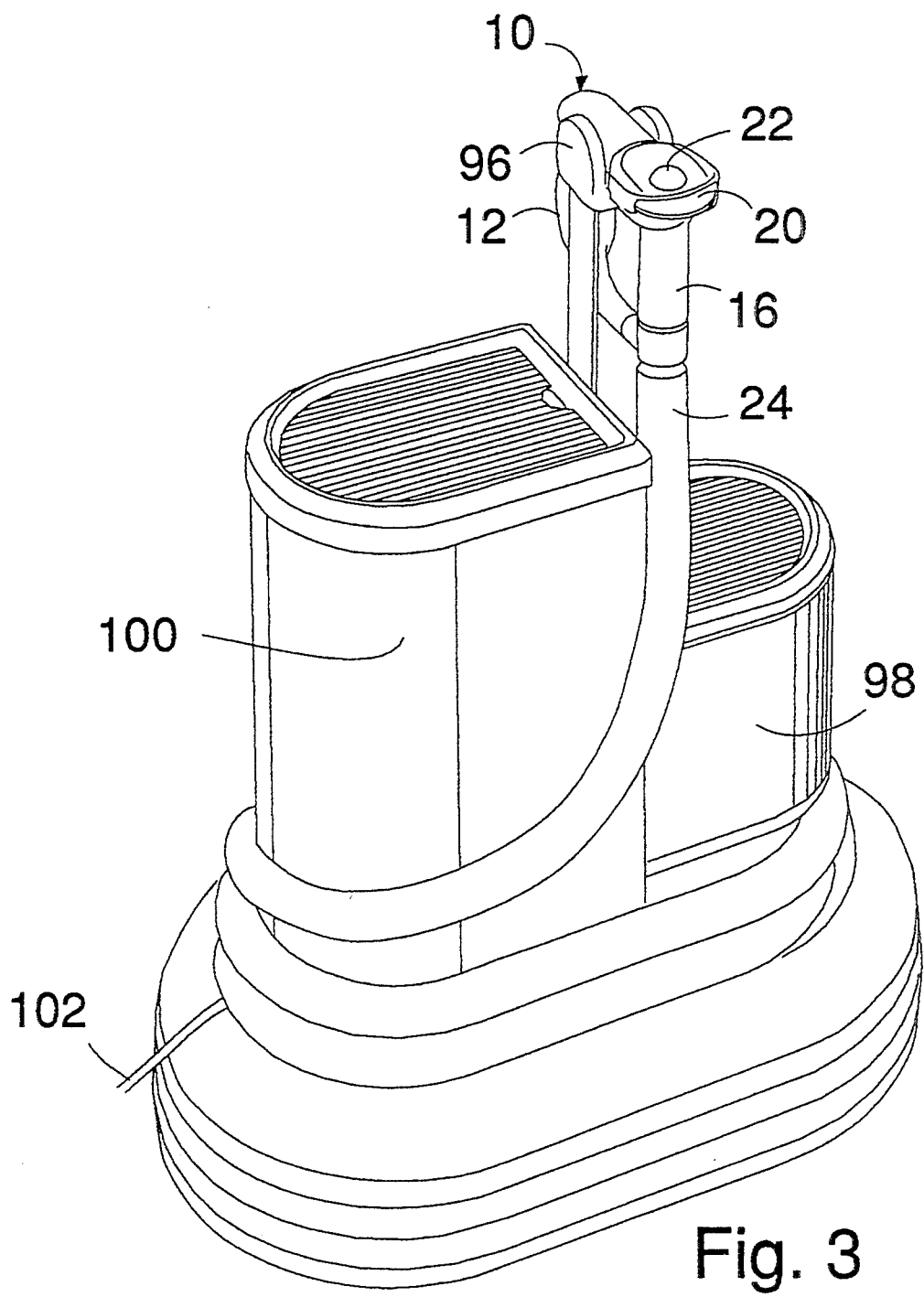
FIG. 3 is a perspective view of a cutting device assembly including a power supply and vacuum system.
Figure 4:
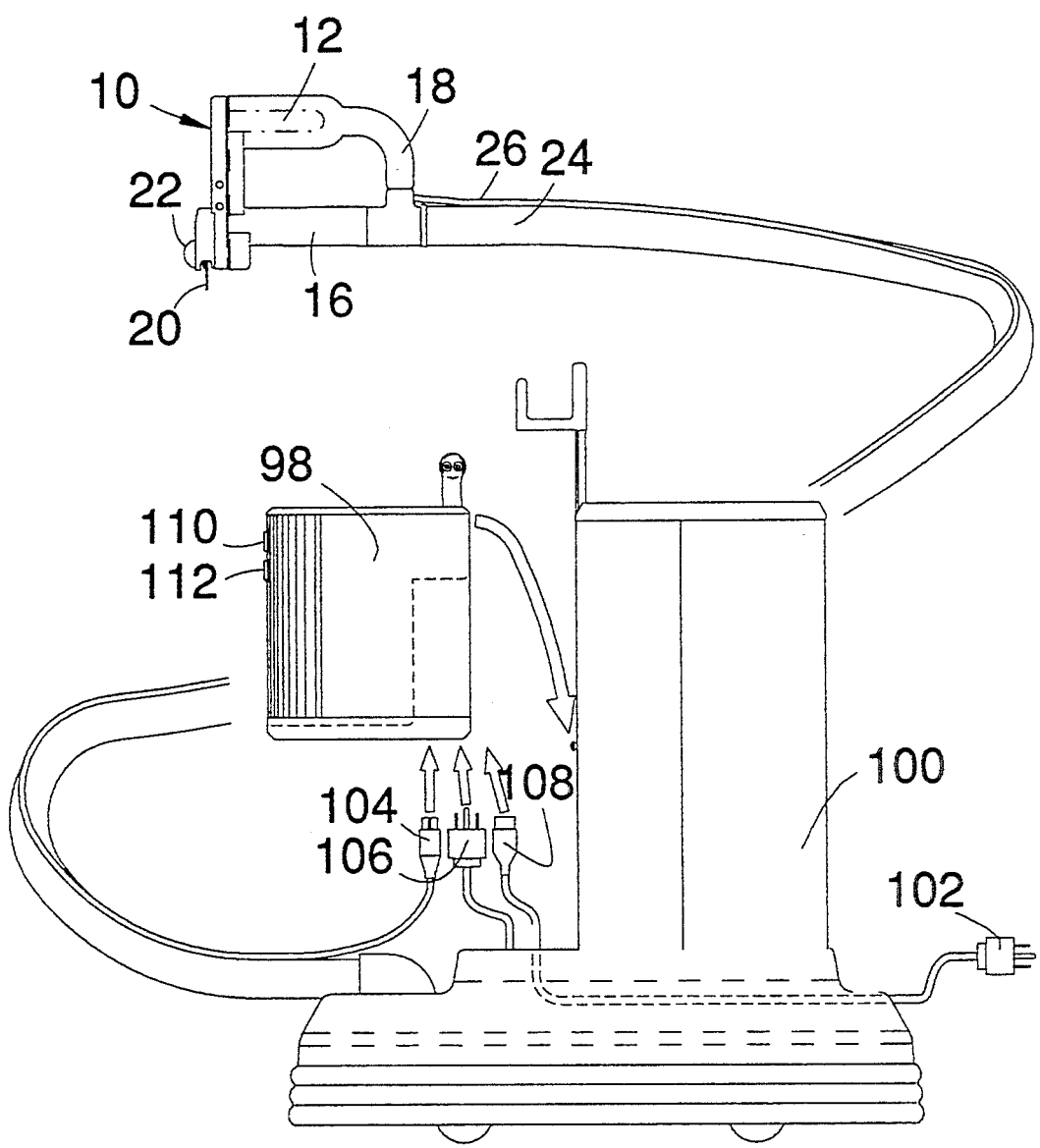
FIG. 4 is a plan view of the physical connections of the cutting device assembly.

An assembly including the cutting device 10 described above is shown in FIG. 3. This assembly includes the cutting device 10 (with motor housing 12, handle 16, cutting blade 20, and blade guard 22), a holder 96, a power supply 98, a vacuum 100, and an A/C inlet 102. The vacuum hose 24 connects the vacuum 100 to the cutting device 10. FIG. 4 shows the physical connections between these members. Also shown in FIG. 4 are the plugs 104, 106, and 108 for the power cable 26, the vacuum 100, and the A/C inlet 102, respectively, which all engage with the power supply 98. The power supply 98 also includes a master switch 110 and a vacuum mode switch 112 by which a user can control whether the cutting device 10 may be turned on and whether a vacuum will be provided with power thereby enabling suction to be provided.

Figure 5:
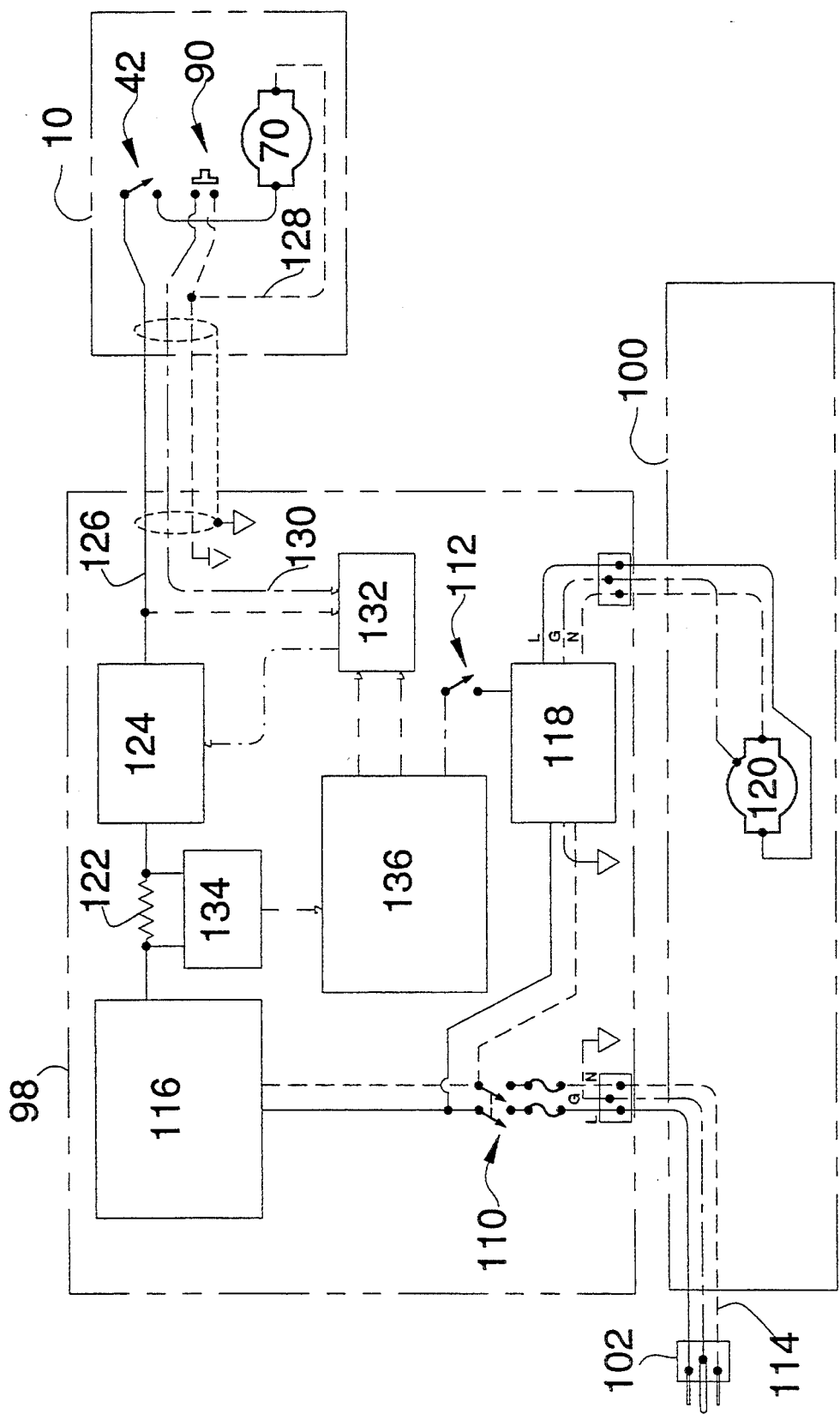
FIG. 5 is a block diagram of the electronic system for powering a cutter motor and vacuum.
Figure 6A:
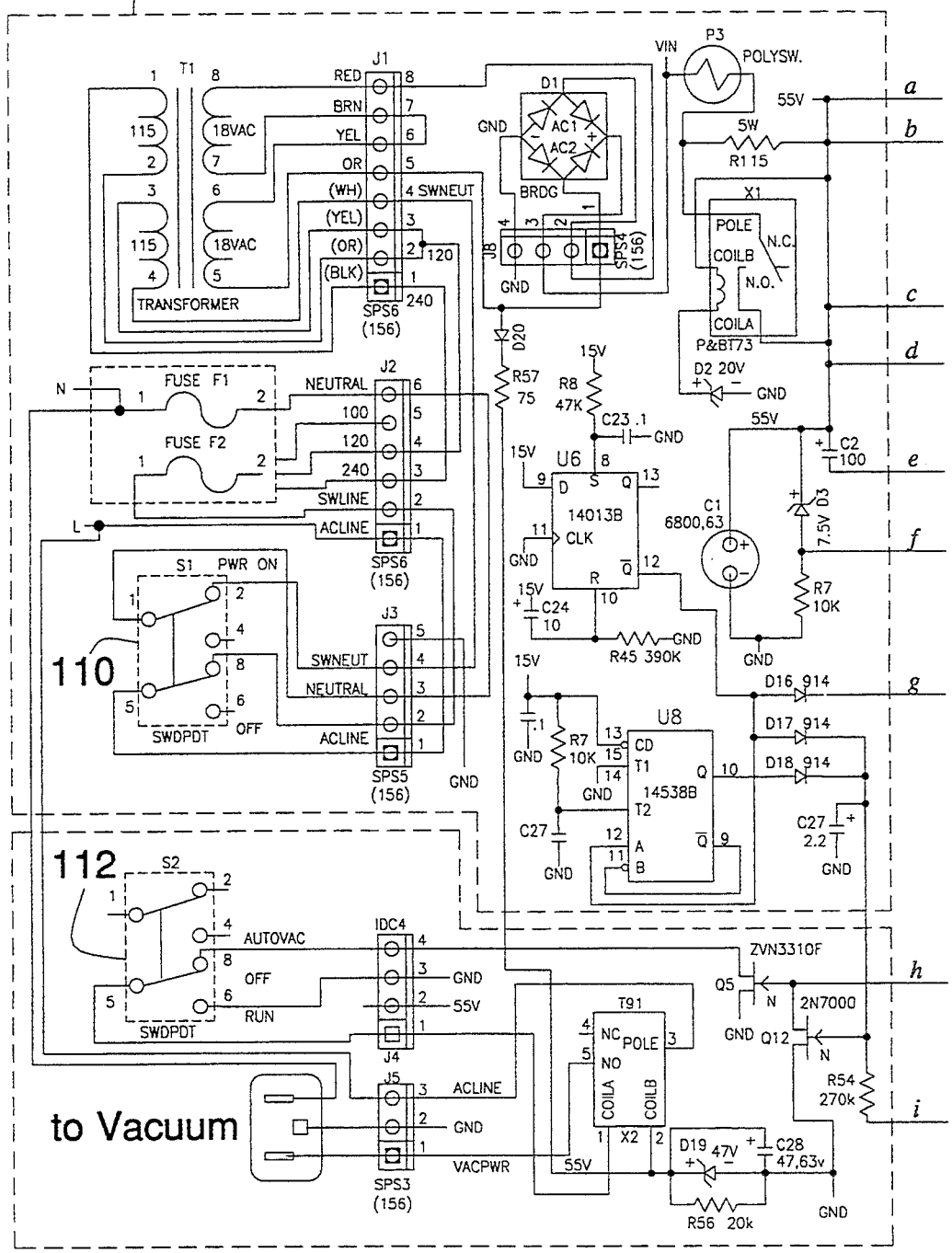
FIG. 6 is a detailed circuit diagram of the system of FIG. 5.
Figure 6B:
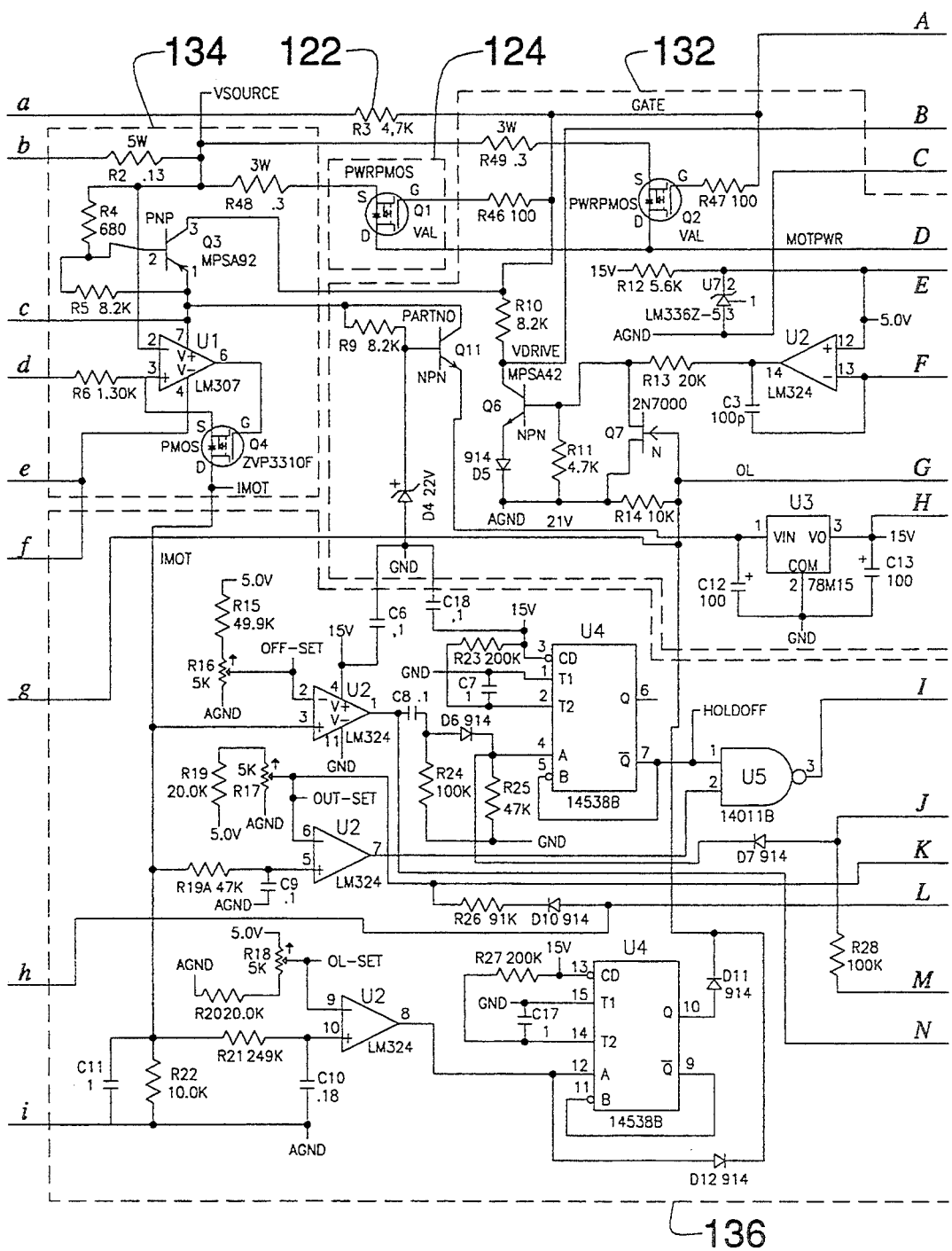
Figure 6C:
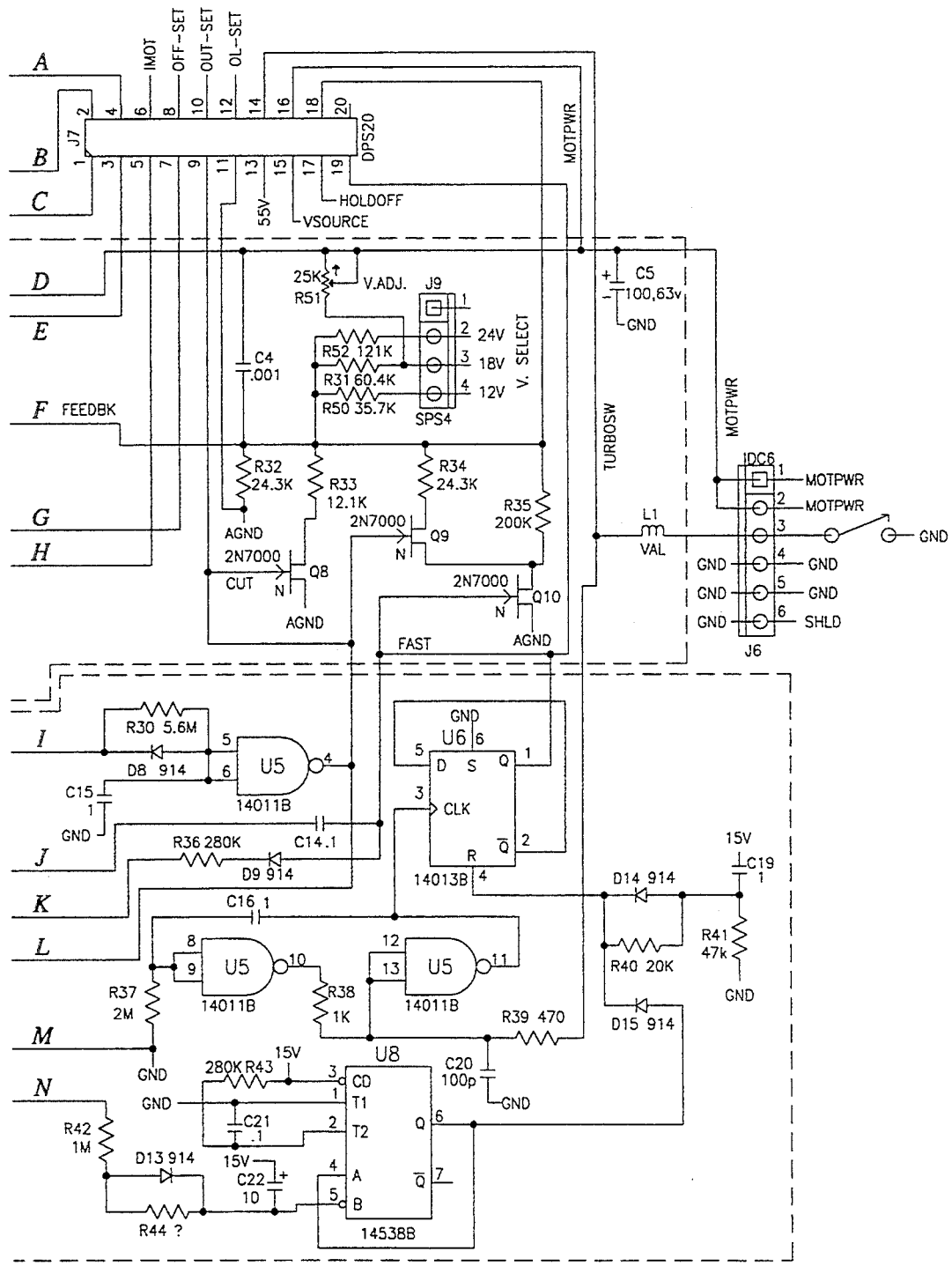

Turning now to the electronic system which powers the motor 70 and the vacuum 100, FIG. 5 shows an overall block diagram, and FIG. 6 shows a detailed circuit diagram thereof. The system includes a power supply 98 shown connected to the cutting device 10 and the vacuum 100. The system is connected to a standard 110–120 volt supply (or standard 220–240 volt supply) via a standard plug 102 and cord 114. The cord 114 is connected to a primary on/off switch 110 which supplies power to the cutting device voltage supply system 116 which comprises a voltage select transformer, rectifier, filter and soft start circuits which are more fully illustrated in FIG. 6 and supplies power to a relay 118 which, in turn, supplies power to an electrical motor 120 in the vacuum 100. The voltage system 116 is connected through a series resistor 122 to a voltage regulator 124 comprising a field effect transistor (FET) series pass regulator and from this regulator through line 126 to the cutting device 10. This line 126 is connected to the on/off switch 42 of the cutting device 10 which is connected to the D.C. motor 70 of the cutting device 10 which, in turn, is connected to a return or ground line 128. The turbo switch 90 is connected through a line 130 to a voltage control 132 which functions to provide a higher voltage to the cutting device motor 70 so as to provide the higher power "turbo" mode discussed earlier.

A current sensing circuit 134 is connected across the series resistor 122 in a conventional manner to sense motor current through the resistor 122. This current sensing circuit 134 is connected to a detector circuit 136 which provides cutter off, cutter on, cut and overload detectors, along with timing and delay circuits, which are more fully illustrated in FIG. 6. This circuit 136 in conjunction with the voltage control 132, current sensing system, 122, 134 and regulator 124 function to first energize the cutter motor 70 in the idle mode by providing a first voltage level, sensing current to the motor 70 when it is loaded (i.e. when a cutting commences) and then providing a higher voltage and thus higher power to the motor, and also to provide the even higher "turbo" power function. Additionally, the circuit 136 senses and provides an appropriate delay to switch the cutting device motor 70 back to the idle mode after cutting is terminated.

A vacuum mode switch 112 is provided between the circuit 136 and the vacuum relay 118. When this switch is in an automatic mode, the vacuum relay is energized to power the vacuum motor 120 when cutting commences (i.e. either in normal cutting mode or turbo mode), and not when in the idle mode.

While an embodiment of the present invention has been shown and described, various modifications may be made without departing from the scope of the present invention, and all such modifications and equivalents are intended to be covered.

We claim:

1. A cutting device for cutting casts and other rigid objects comprising
    a handle in close proximity to, connected to and for directing an oscillating cutting blade, wherein the oscillating cutting blade defines an axis of rotation,
    a motor for driving the oscillating cutting blade, the motor having an axis of rotation substantially parallel to the blade axis of rotation and being mechanically coupled to the oscillating cutting blade and providing a mass positioned offset approximately three inches or more from said blade axis of rotation and substantially parallel to the handle, and
    a housing to which the handle, the cutting blade, and the motor are supportably attached, the cutting blade being positioned closer to the handle than to the motor.

2. The cutting device of claim 1 wherein the device has a moment of inertia and wherein the offset positioning of the motor increases the moment of inertia about the axis of rotation.

3. The cutting device of claim 2 wherein the housing offsets the motor from the axis of rotation.

4. The cutting device of claim 2 wherein the motor comprises a D.C. motor.

5. The cutting device of claim 2 further comprising a dynamic braking system for the motor.

6. The cutting device of claim 1 wherein the motor comprises a D.C. motor.

7. The cutting device of claim 1 further comprising a dynamic braking system for the motor.

8. A cutting device for cutting casts and other rigid objects comprising a handle in close proximity to, connected to and for directing an oscillating cutting blade, wherein the oscillating cutting blade defines an axis of rotation, and a motor having an axis of rotation and coupled to and for driving the oscillating cutting blade, wherein the motor is positioned offset approximately three inches or more from and its axis of rotation is substantially parallel to the axis of rotation of the oscillating blade, and the cutting blade is positioned closer to the handle than to the motor.

9. The cutting device of claim 8 further comprising a dynamic braking system for the motor.

10. A cutting device for cutting casts and other rigid objects comprising a handle in close proximity to, connected to and for directing an oscillating cutting blade, and wherein the oscillating cutting blade defines an axis of rotation, and a motor for driving the oscillating cutting blade, the motor having an axis of rotation substantially parallel to the blade axis of rotation and being mechanically coupled to the oscillating cutting blade, wherein the motor is positioned offset approximately three inches or more from and substantially parallel to the handle when the device is positioned to cut thereby providing space between the motor and the handle such that a user's hand could grasp the handle and such that the device has a center of gravity located between the handle and the motor, and a housing to which the handle, the cutting blade, and the motor are supportably attached, the cutting blade being positioned closer to the handle than to the motor.

11. A cutting device for cutting casts and other rigid objects comprising a hollow handle having a substantially unobstructed cross section, connected to and for directing an oscillating cutting blade and connected to a vacuum source, wherein the cutting blade defines an axis of rotation, a motor offset from the handle wherein the motor is mechanically coupled to the oscillating cutting blade and connected to the vacuum source, and mechanical components connecting the motor to the cutting blade are encased in a housing, and an airflow channel extending from the vacuum source to an intersection wherein the channel splits to extend to the hollow handle enabling suction to be supplied at the cutting blade to vacuum cutting debris and enabling airflow to be directed past the cutting blade and through the handle to cool the cutting blade and the handle, and to extend to the motor enabling airflow to be directed past the motor to cool said motor.

12. A cutting device for cutting casts and other rigid objects comprising a cutting blade adapted to be oscillated, the cutting blade having an axis of rotation, a handle disposed in close proximity to and for supporting the cutting blade, the handle allowing the blade to be directed by a user's hand when grasping the handle, and a motor coupled to the cutting blade by a linkage for driving and causing the cutting blade to oscillate, the motor having an axis substantially parallel to and offset from the axis of the cutting blade by a distance sufficient to provide a space between the motor and handle to readily allow a user's hand to grasp the handle, and the cutting blade is positioned closer to the handle than to the motor.

13. The cutting device as in claim 12 wherein the motor is an electrical motor, the axes of the cutting blade and motor are displaced approximately three inches or more, and the handle is substantially hollow to allow suction therethrough of material cut by the cutting blade.

14. A cutting device for cutting casts and other rigid objects comprising a motor housing containing a motor, a front housing, a handle, with the motor housing, front housing, and handle essentially defining a generally rectangular shape, with the motor housing and handle forming a top and bottom, respectively, of the rectangle and the front housing connected between the motor housing and handle and forming an end of the rectangle, a cutting blade disposed proximate the junction of the front housing and handle, the cutting blade having an axis of rotation essentially parallel to the handle, and the handle serving to allow the blade to be directed by a user's hand grasping the handle, and the motor being coupled to the cutting blade for driving and causing the cutting blade to move, the motor having an axis substantially parallel to and generally offset from the axis of the cutting blade by a distance sufficient to provide a space between the motor housing and the handle to readily allow a user's hand to grasp the handle.

15. A cutting device for cutting casts and other rigid objects comprising a hollow handle having a substantially unobstructed cross section, in close proximity to, connected to and for directing an oscillating cutting blade and connected to a vacuum source for drawing air through the handle, wherein the cutting blade defines an axis of rotation, and a motor offset from the handle wherein the motor is mechanically coupled to the oscillating cutting blade and connected to the vacuum source for drawing air past the motor, and mechanical components connecting the motor to the cutting blade are encased in a housing.

16. The cutting device of claim 15 wherein the device has a moment of inertia and the offset position of the motor increases the moment of inertia about the axis of rotation.

17. The cutting device of claim 15 further including a dynamic braking system for the motor.

18. The cutting device of claim 15 further comprising a vacuum hose which with the hollow handle provide a substantially unobstructed airflow channel from the cutting blade to the vacuum source.

19. A cutting device for cutting casts and other rigid objects comprising a handle in close proximity to, connected to and for directing an oscillating cutting blade, wherein the oscillating cutting blade defines an axis of rotation, a motor for driving the oscillating cutting blade, the motor having an axis of rotation substantially parallel to the blade axis of rotation and being coupled to the oscillating cutting blade by a crank, the axis of rotation of said motor being spaced from said handle, a mass positioned offset approximately three inches or more from the blade axis of rotation and substantially parallel to the handle, and a housing to which the handle, the cutting blade, and the mass are supportably attached, the cutting blade being positioned closer to the handle than to the mass.

20. The cutting device of claim 19 wherein the device has a moment of inertia and wherein the offset positioning of the mass increases the moment of inertia about the axis of rotation.

* * * * *